(12) United States Patent
Alexander

(10) Patent No.: US 6,561,802 B2
(45) Date of Patent: May 13, 2003

(54) DEVICE FOR IDENTIFYING CARIES, PLAQUE, BACTERIAL INFECTION, CONCRETIONS, TARTAR AND OTHER FLUORESCENT SUBSTANCES ON TEETH

(75) Inventor: Hack Alexander, Biberach-Rissegg (DE)

(73) Assignee: Kaltenbach & Voigt GmbH & Co., Biberach (DE)

( * ) Notice: Subject to any disclaimer, the term of this patent is extended or adjusted under 35 U.S.C. 154(b) by 0 days.

(21) Appl. No.: 09/810,592

(22) Filed: Mar. 16, 2001

(65) Prior Publication Data

US 2001/0023057 A1 Sep. 20, 2001

(30) Foreign Application Priority Data

Mar. 17, 2000 (DE) .......................... 100 13 210

(51) Int. Cl.[7] ................................. A61C 1/00
(52) U.S. Cl. ........................................ 433/29
(58) Field of Search .................. 433/29, 215, 229; 356/317, 318, 341; 600/411, 410, 476, 477

(56) References Cited

U.S. PATENT DOCUMENTS

| | | | | |
|---|---|---|---|---|
| 4,479,499 A | * | 10/1984 | Alfano ........................ | 433/29 |
| 5,178,536 A | * | 1/1993 | Werly et al. ................. | 433/29 |
| 5,306,144 A | * | 4/1994 | Hibst et al. .................. | 433/29 |
| 5,328,365 A | * | 7/1994 | Jacoby ........................ | 433/29 |
| 5,382,163 A | * | 1/1995 | Putman ...................... | 433/215 |
| 5,702,249 A | * | 12/1997 | Cooper ....................... | 433/29 |
| 5,894,620 A | * | 4/1999 | Polaert et al. ................ | 433/29 |
| 6,007,333 A | | 12/1999 | Callan et al. ................. | 433/29 |
| 6,024,562 A | | 2/2000 | Hibst et al. .................. | 433/29 |
| 6,053,731 A | | 4/2000 | Heckenberger ............. | 433/29 |
| 6,095,810 A | * | 8/2000 | Bianchetti ................... | 433/29 |
| 6,102,704 A | | 8/2000 | Eibofner et al. ............. | 433/215 |
| 6,135,774 A | | 10/2000 | Hack et al. .................. | 433/215 |
| 6,384,917 B1 | * | 5/2002 | Fradkin ....................... | 433/29 |

FOREIGN PATENT DOCUMENTS

| | | | |
|---|---|---|---|
| DE | 83 22 850 U1 | 10/1987 | ........... A61C/17/00 |
| DE | 195 41 686 A1 | 5/1997 | ........... A61C/19/04 |
| DE | 297 04 185 U1 | 6/1997 | ........... A61C/19/04 |
| DE | 297 05 934 U1 | 7/1997 | ........... A61C/19/04 |
| DE | 197 42 701 A1 | 4/1998 | ........... A61C/17/02 |
| DE | 197 09 500 C1 | 7/1998 | ........... A61C/19/04 |

OTHER PUBLICATIONS

English language abstract of DE 197 09 500 C1.
English language abstract of DE 197 42 701 A1.
English language abstract of DE 297 15 934 U1.
English language abstract of DE 195 41 686 A1.
English language abstract of DE 297 04 185 U1.
European search report dated Sep. 28, 2000, 2 pages.

* cited by examiner

*Primary Examiner*—Todd E. Manahan
(74) *Attorney, Agent, or Firm*—Marshall, Gerstein & Borun

(57) ABSTRACT

A device is disclosed for identifying caries, plaque, bacterial infection, concretions, tartar and other fluorescent substances on teeth. The device has means for generating stimulating radiation which is to be directed onto a tooth-tissue region that is to be investigated. The device also has detection means and evaluation means for detecting and evaluating fluorescent radiation that is generated by the irradiated tooth-tissue region in response to the irradiation. A beam splitter, which is arranged in the optical path between the means for generating the stimulating radiation and the tooth-tissue region to be investigated and which reflects the stimulating radiation in the direction of the tooth-tissue region and substantially lets through the fluorescent radiation, is formed by the planar rear side of a substantially hemispherical lens. In this way a more compact optical diagnostic device is rendered possible.

34 Claims, 6 Drawing Sheets

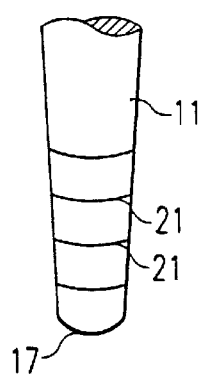 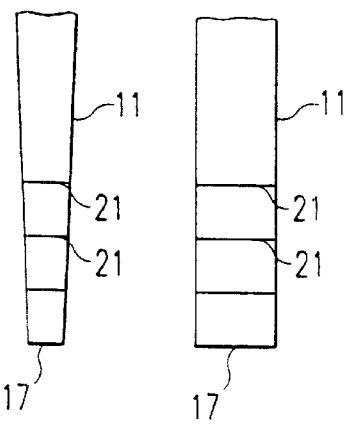
Fig. 5  Fig. 6a  Fig. 6b
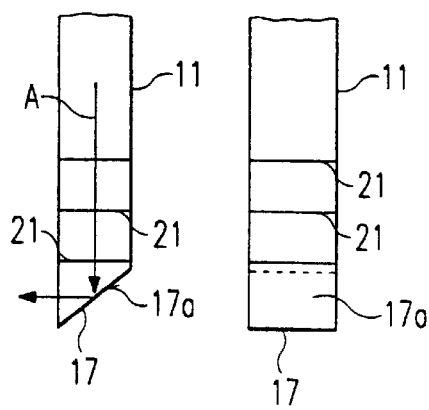 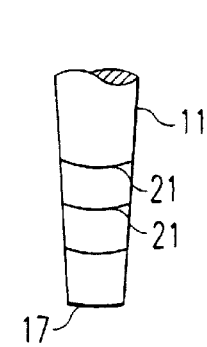
Fig. 7a  Fig. 7b  Fig. 8
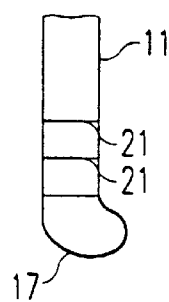
Fig. 9

DEVICE FOR IDENTIFYING CARIES, PLAQUE, BACTERIAL INFECTION, CONCRETIONS, TARTAR AND OTHER FLUORESCENT SUBSTANCES ON TEETH

FIELD OF THE INVENTION

The present invention relates to a device for identifying caries, plaque, bacterial infection, concretions, tartar and other fluorescent substances on teeth.

BACKGROUND OF THE INVENTION

Such devices, with the aid of which it is possible to ascertain the presence of caries on teeth in a non-contacting manner, have been proposed repeatedly recently. In this connection, a tooth-tissue region that is to be investigated is irradiated with—in the ideal case—a monochromatic light source and fluorescent radiation is generated at the irradiated region in response thereto. This fluorescent radiation is subsequently evaluated, making use of the fact that the fluorescence spectrum of a carious tooth-tissue region is significantly different from the corresponding spectrum of a healthy tooth-tissue region. Thus, for example, in the red spectral range (approximately 550 to 650 nm) of a tooth that is infected by caries or plaque the intensity of fluorescence is clearly higher than in the case of a healthy tooth. By means of suitable detection and evaluation, a carious tooth-tissue region can thus be unequivocally distinguished from a healthy tooth-tissue region with the aid of a simple and non-contacting method of investigation.

Devices of this kind are described, for example, in DE 297 04 185 U1 or DE 197 09 500 C1. In the first instance they have a facility for generating the stimulating radiation, for example an HeNe-laser which generates stimulating radiation with a wavelength in the range between 600 nm and 670 nm. The stimulating radiation is coupled into a light-guide system by way of an optical system, which consists of a plurality of lenses or mirrors, and is directed through said light-guide system onto the tooth-tissue region that is to be investigated. In the case of the device described in DE 197 09 500 C1, the light-guide system consists of a light-guide that extends from the light source as far as the tip of a handpiece and provided at the end of which there is a light probe by means of which the light is coupled out and directed onto the desired region. The fluorescent radiation that results at the irradiated tooth-tissue region is coupled back into the light-guide system by way of the tip of the light probe and transmitted to a detecting device. Since the light-guide system is usually used to transmit both the stimulating radiation and the fluorescent radiation simultaneously, a beam splitter is located in the optical path between the stimulating-radiation source and the tooth-tissue region that is to be investigated in order to separate the two types of radiation from each other and to supply the fluorescent radiation to the detection means.

The elements of the optical diagnostic device previously described, in particular the means for generating the stimulating radiation and the optical system including the beam splitter for coupling the stimulating radiation into the light-guide system or for coupling the fluorescent radiation out, are of a certain size so that previously it was usual to arrange these elements in a central unit and to transmit the two types of radiation to or from the dental handpiece with the aid of a supply tube in which one or more light-guides are arranged.

SUMMARY OF THE INVENTION

It is the object of the present invention to improve the known devices for identifying caries, plaque, bacterial infection, concretions, tartar and other fluorescent substances on teeth in such a way that they can be realized in a comparatively simple and space-saving manner in terms of their structure.

This object is achieved generally in accordance with the invention by means of integration of components.

The object is achieved in accordance with one aspect of the invention by means of a device that is distinguished by the fact that a beam splitter, which is disposed in an optical path between a means for generating a stimulating radiation and a tooth-tissue region that is to be investigated, is formed by a planar rear side of a substantially hemispherical lens. This planar rear side is formed in such a way that the stimulating radiation is reflected in a direction of the tooth-tissue region that is to be investigated, whilst a fluorescent radiation, on the other hand, passes through it substantially without hindrance. Since a curved front side of the hemispherical lens simultaneously has a focusing effect, with the aid thereof it is possible to couple the stimulating radiation into a light-guide system and thereby possibly dispense with additional optical means therefor. The development of the optical diagnostic device in accordance with the invention is thus distinguished by its simple structure and the possibility connected therewith of being able to configure it with great indifference to outside influences. Thus the possibility additionally exists as well of arranging the important elements of the device not as before in a central unit that is separate from the handpiece, but directly in the handpiece itself.

The beam-splitting effect of the planar side of the hemispherical lens is preferably achieved in that the latter has a coating which reflects light at the frequencies of the stimulating radiation and lets through without hindrance light in the frequency range of the fluorescent radiation that is generated. There is preferably an optical filter adjacent to the planar side of the hemispherical lens in order to filter out in a better way those portions that are not required for the detection and assessment of the fluorescent radiation and which might possibly constitute a disturbance. A laser diode is preferably used in order to generate the stimulating radiation, since this only has very small dimensions and consequently can easily be integrated into a handpiece. Furthermore, the detection means can have a photodiode that is arranged behind the optical filter for the purpose of detecting the fluorescent radiation.

The way in which the stimulating radiation of the light source is directed onto the tooth-tissue region that is to be investigated is dependent upon the field of application of the optical diagnostic method. A plurality of possibilities for this are discussed in the following.

The device in accordance with the invention can, for example, be used in a very advantageous manner in periodontal diagnostics. For this, provided at the head end of the handpiece there is an optical probe which is inserted into the tooth pocket of a tooth that is to be investigated. At the tip of the probe the stimulating radiation is coupled out and directed onto the tooth-tissue region that is to be investigated. As previously described, the fluorescent radiation that results at the irradiated tooth-tissue region is also coupled back into the light-guide system with the aid of the optical probe and directed onto the hemispherical lens, acting as a beam splitter, and onto the means for evaluating the fluorescent radiation. As a result, the possibility exists of also being able to assess the region of a tooth stump, which is usually difficult to access and consequently difficult to investigate, with the aid of the simple, yet effective optical diagnostic method.

The probe preferably consists of a light-guiding material and in this connection has the form of a cone, a light wedge or a periodontal probe. In order to be able to obtain more detailed information on the depth of the tooth pocket, furthermore the probe can have markings or a scale on its outside. Furthermore, the tip of the probe is preferably mounted on the handpiece in a resilient manner in order to give the user the possibility of proportioning the probing force and consequently avoiding damage to the patient's gum. The types of radiation can be transmitted from the hemispherical lens to the optical probe or in the opposite direction by means, for example, of a mirror that is arranged above the probe or a flexible light-guide that is connected to the end of the probe.

As has been explained before, an important advantage of the diagnostic device in accordance with the invention can be seen in the fact that it can be configured in an extremely compact manner in terms of its dimensions on account of the integration of the components. The possibility consequently exists of supplementing known dental handpieces for treating a tooth-tissue region by the optical diagnostic method and consequently of providing a combined diagnostic and treatment device. In this connection, previously it was merely known that laser-treatment units could be supplemented by the optical diagnostic method, since the light-guides present for the transmission of the laser-treatment radiation could also be utilized in a simple manner by the diagnostic system. Such a diagnostic and treatment device using laser radiation is described, for example, in DE 297 05 943 U1.

In accordance with the present invention, however, a dental device having a handpiece for the mechanical treatment of the tooth-tissue region is supplemented by the optical diagnostic method. This dental device can, for example, be a tartar-removing unit, as described in DE 83 22 850 U1, or a handpiece in which the treatment of the tooth-tissue region is effected by means of an abrasive treatment agent, as described, for example, in DE 197 42 701 A1. In the case of these known dental devices, the handpieces are as a rule filled up by the drive devices that are arranged in them for the treatment tips or transmission channels for treatment media or the like in such a way that previously it was not possible to integrate an optical diagnostic device therein as well without having to justify a further enlargement of the handpiece. These difficulties are now overcome by means of the device in accordance with the invention so that a very effective and versatile dental device can be formed. In the case of the tartar-removing unit or the hand instrument for treatment by means of an abrasive fluid, the light-guide that is required for the transmission of the radiation types can, for example, extend within the instrument tip or on the outside thereof. The possibility then exists of equipping the arrangement with an indicating device which directly intimates to the user whether the tooth-tissue region, to which the tip of the instrument is directed, is carious or loaded with concretions or films or not so that the user can match his treatment to the result of diagnosis. Furthermore, the possibility can also be provided for a control device to control the mechanical treatment automatically as a function of the result of diagnosis.

BRIEF DESCRIPTION OF THE DRAWINGS

The invention shall be explained in greater detail in the following with reference to the enclosed drawings in which:

FIGS. 5 to 9 show a plurality of exemplary embodiments of the optical probe;

FIG. 12b shows an enlarged representation of the tip of the instrument that is shown in FIG. 12a.

DETAILED DESCRIPTION OF THE PREFERRED EMBODIMENTS

Figure 1:
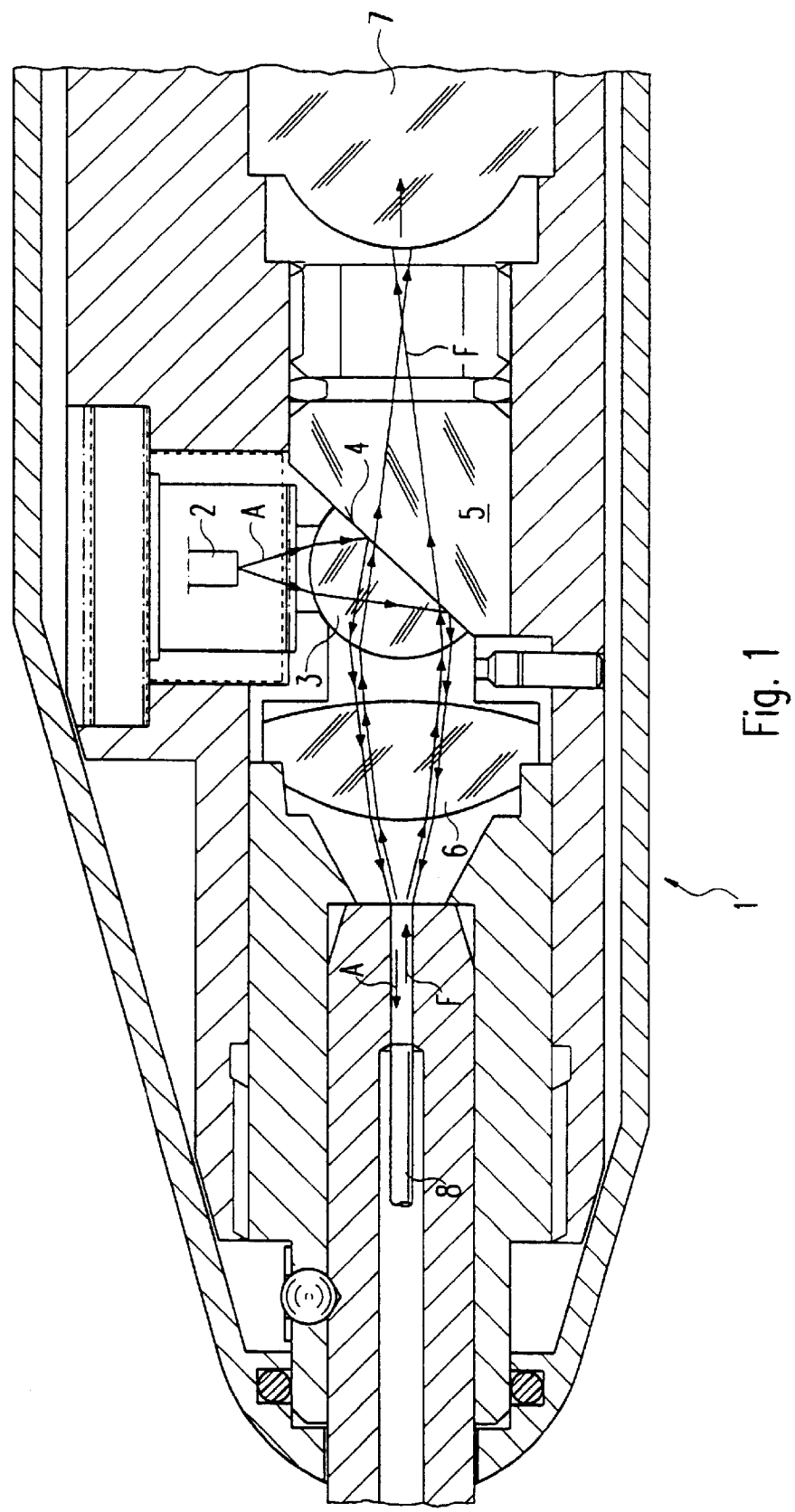
FIG. 1 shows the device in accordance with the invention for identifying caries, plaque or bacterial infection on teeth.

The arrangement of the optical diagnostic device within a handpiece shall now be explained in the first instance with reference to FIG. 1. The handpiece 1 is a dental handpiece which is not defined in greater detail in the first instance and which, on the one hand, may be used exclusively for diagnostic purposes but, on the other hand, may also—as is explained later with reference to two examples—comprise further elements for the therapeutic treatment of the tooth-tissue region under investigation. Located as a light source for the stimulating radiation A in the upper region of the handpiece 1 there is a laser diode 2, which generates stimulating radiation in the range between 600 nm and 670 nm. The stimulating radiation preferably has a wavelength of approximately 655 nm, since here the best possible compromise between the output of the laser diode 2 and the spectral difference between the stimulating radiation A and the fluorescent radiation F is attainable.

The stimulating radiation A that is radiated out from the laser diode 2 enters the hemispherical lens 3 that is arranged below the laser diode 2 and is reflected on the planar rear side 4 in the direction of the front end of the handpiece 1. The reflection of the stimulating radiation A is thereby effected by a coating which is vapour-deposited onto the planar rear side 4 of the hemispherical lens 3 and which effectively reflects light in the frequency range previously mentioned. Upon exit from the hemispherical lens 3 the stimulating radiation A is directed through the curved front side onto an additional focussing lens 6 that is arranged in front of it and through which the stimulating radiation A is finally coupled into a light-guide 8 which extends to the front end of the handpiece 1. The light-guide 8 leads to an optical probe (not shown), an element for coupling light out, or further optical elements with the aid of which the stimulating radiation A is directed onto the tooth-tissue region that is to be investigated.

The fluorescent radiation F that results in response to the irradiation at the tooth-tissue region is transmitted in the opposite direction by way of the light-guide 8 back again to the focussing lens 6 and the hemispherical lens 3. The fluorescent radiation F, whose wavelength is greater than that of the stimulating radiation A, is now no longer reflected at the planar rear side 4 of the hemispherical lens 3 though, but passes through it without hindrance into an optical filter 5 that is arranged directly behind the hemispherical lens 3. The blocking range of this filter 5 lies in the wavelength range of the stimulating radiation A in order to eliminate portions of the stimulating radiation A that possibly pass through the rear side 4 of the hemispherical lens 3. Finally, arranged downstream of the optical filter 5 there is a photodiode 7, which is part of the means for detecting the fluorescent radiation F and for evaluating the latter. The evaluation of the intensity of the fluorescent radiation F or the assessment whether the tooth-tissue region under investigation has caries or is loaded with concretions or films is effected either directly in the handpiece 1 or a signal corresponding to the intensity of the fluorescent radiation F is transmitted to a central unit.

The light-guide 8 can, in a known manner, be a bundle of a plurality of fibre optical light-guides, arranged along the length of which there is one fibre for the transmission of the stimulating radiation A that is surrounded by a plurality of fibre optical light-guides for detecting the fluorescent radiation F. The focussing effect of the curved surface of the hemispherical lens 3 depends in the first instance upon the size and the radius of the lens 3. Given a suitable choice of the dimensions for the hemispherical lens 3 it is also possible to dispense with the additional focussing lens 6, whereby the optical device can be configured even more simply.

As can be inferred from FIG. 1, the device consists of only very few optical elements so that on the one hand it can be produced inexpensively, yet on the other hand is also less susceptible to jolts or changes in temperature than the diagnostic device known previously.

Figure 2:
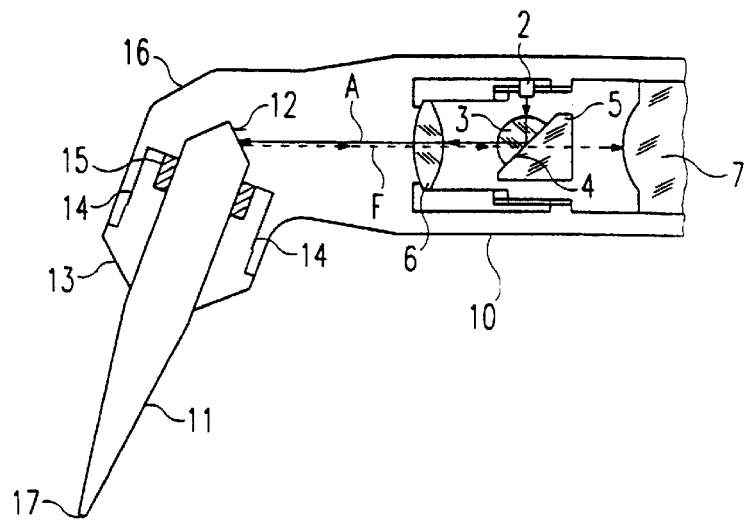
FIG. 2 shows the integration of the device in accordance with the invention in a dental handpiece for periodontal diagnostics.

A device for periodontal diagnostics shall now be presented as a first exemplary embodiment. Previously, merely laser-treatment instruments were known, arranged at the head end of which there is a decoupling element that is arranged at an angle to the longitudinal axis of the handpiece in the form of a periodontal probe which can be inserted into the pocket between a tooth stump and the gum for the treatment of the tooth, tooth film or gum there. Such a treatment instrument is described, for example, in DE 196 36 265 A1. FIG. 2 shows a modification in accordance with the invention of the treatment instrument described in the above mentioned Offenlegungsschrift to form a device for periodontal diagnostics. For this purpose, the optical diagnostic device explained with reference to FIG. 1—the same elements have the same reference symbols here—has been integrated into the handpiece 10.

The handpiece 10 has at its front end a head portion 16 in which an optical probe 11 that is mounted at an angle to the longitudinal axis of the handpiece 10 is arranged. The optical probe 11 is mounted by way of a screw insert 13 which can be connected to the head portion 16 by way of a thread 14, with a holding projection 15, which is arranged on the outside of the probe 11, being enclosed in a corresponding recess of the screw insert. This construction presents the possibility of replacing the probe 11 quickly and simply with a new probe which, for example on account of being of a different shape, is better suited for the new investigation purpose.

The stimulating radiation A is coupled in with the aid of the additional focussing lens 6 which focusses the radiation onto a conical end face 12 of the optical probe 11. The shape and the material of the probe 11 are selected in such a way that the radiation that is coupled in by way of the end face 12 is reflected totally within the probe 11 and merely emerges at the latter's lower tip 17. As is explained further later, the tips can be adapted to the respective region that is to be investigated.

The fluorescent radiation F that results directly in front of the probe tip 17 is directed further in opposition to the stimulating radiation A by means of total reflection within the probe 11 as far as the latter's upper end face 12 and from there is projected onto the focussing lens 6, after which it is directed onto the photodiode in a known manner by way of the hemispherical lens 3 and the optical filter 5. The probe 11 can be made of a material that is permeable to light, such as, for example, glass or quartz or plastics material. On account of its small dimensions and shapes it is suitable in particular for insertion into tooth pockets between the gum and the base of the tooth.

Figure 3:
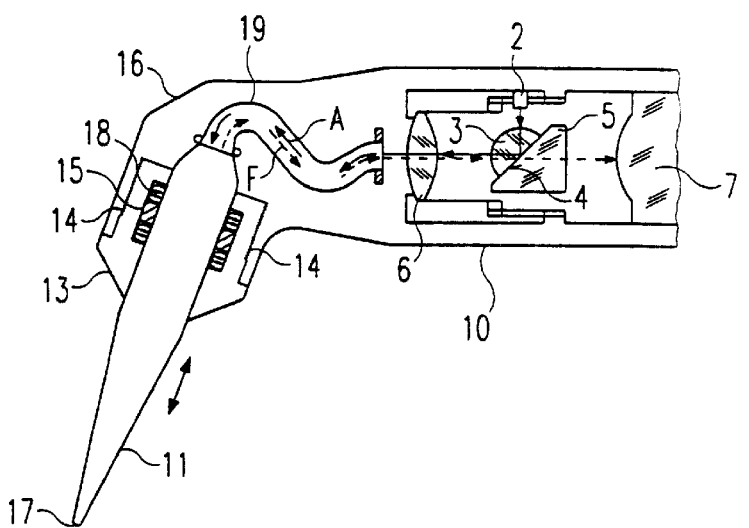
FIGS. 3 and 4 show further developments of the diagnostic device shown in FIG. 2 with a probe that is mounted in an axially resilient manner.

FIG. 3 shows a further development of the handpiece 10 that is shown in FIG. 2, the substantial difference being that the probe 11 is now no longer mounted in the head portion 16 in a rigid manner, but is mounted so as to be resilient in the axial direction. This is achieved in that the holding projection 15 is of a smaller dimension than the corresponding recess of the screw insert 13 and as a result can be displaced in an axial direction. In order to achieve a central position of the probe 11 in the absence of a force, spring elements 18 are provided above and below the holding projection 15. The resilient mounting of the probe 11 gives the user the possibility of proportioning the probing force, that is, the force with which the probe 11 is inserted into the tooth pocket that is to be investigated, more finely and consequently of avoiding unnecessary injuries to the patient's gum. In order to make it possible to couple the two kinds of radiation in and out effectively in each position of the probe 11, this time a flexible light-guide 19 is used between the focussing lens 6 and the upper side of the probe 11. As an alternative to the mounting that is shown, one single spring element could also be used, arranged above the holding projection 15, since the probe 11 as a rule is merely loaded under pressure and a central position is not absolutely necessary.

Figure 4:
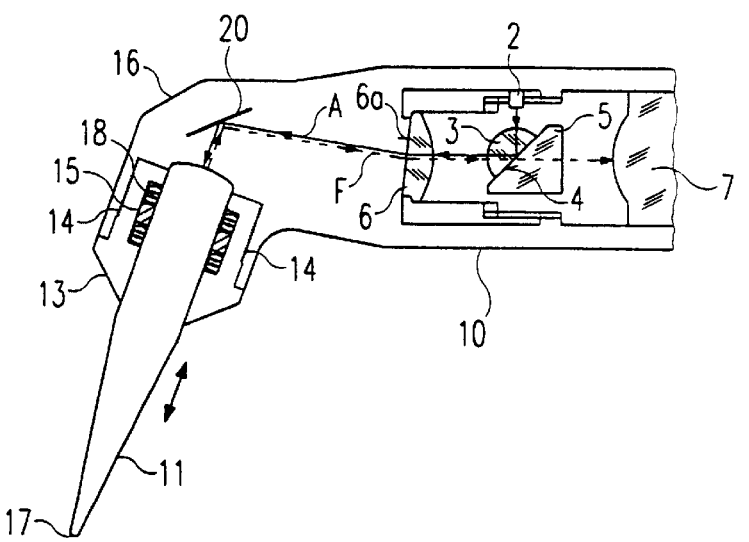

In the exemplary embodiment that is shown in FIG. 4, the probe 11 is mounted in an axially resilient manner in the same way as it is in FIG. 2. However, a flexible light-guide 19 is not used now, coupling-in of the stimulating radiation A being effected here by way of a mirror 20 that is arranged in the head portion 16 in the axial direction above the probe 11. To this end, the front side 6a of the focussing lens 6 facing the head portion 16 of the handpiece 10 is planar and inclined slightly in order to deflect the stimulating radiation onto the mirror 21.

FIGS. 5 to 9 show different possibilities of configuration of the probe 11. In this connection, in each case the lower end of the probe 11 is shown, the more precise configuration of the upper end being determined by the holding support of the probe 11 within the head piece 16 or the means for transmitting the stimulating radiation A and the fluorescent radiation F. The probe 11, which is shown in FIG. 5, is slightly conical in its lower region and has a rounded-off probe tip 17. From this tip 17 upwards at regular intervals there are markings 21 which, after the probe 11 has been inserted into the tooth pocket, provide information on how deep the pocket is and how far the probe 11 has already been inserted. The markings 21 can, for example, be notches or even rings printed thereon that completely surround the probe 11 and consequently are visible from any direction.

The probe 11 that is shown in FIG. 6a in a lateral view has the form of a wedge that tapers towards the tip 17. According to the front view in FIG. 6b, the width of the wedge remains unchanged over its height. As in the case of the probe 11 that is shown in FIG. 5 as well, the stimulating radiation is coupled out at the probe tip 17 and the fluorescent radiation is coupled back into the probe 11 by way of the probe tip 17. The wedge form thereby facilitates the insertion of the probe into the tooth pocket. The height markings 21 previously mentioned are also provided here as well.

The probe 11 that is shown in FIGS. 7a and 7b has the form of a light wedge with an inclined surface 17a which is located at the tip 17 and by way of which the stimulating radiation is coupled out not in an axial direction, but perpendicularly thereto. This enables there to be a diagnosis of the tooth-region surfaces which are arranged at the side close to the probe.

In accordance with FIGS. 8 and 9 further configuration possibilities for the probe 11 consist in a truncated stump (FIG. 8) with a possibly rounded edge at the end face of the probe tip 17 or in a probe 11 with an offset probe tip 17 for access to furcations (FIG. 9).

Figure 10:
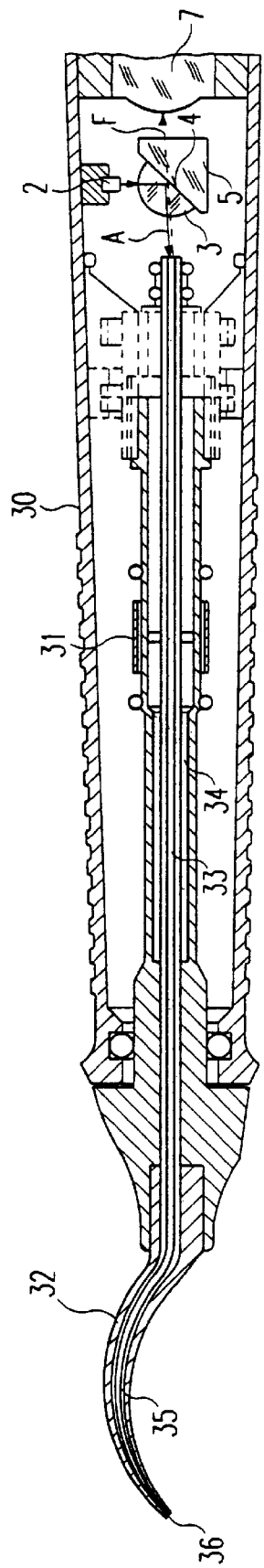
FIG. 10 shows the integration of the optical diagnostic device in a tartar-removing unit.

Finally, the supplement of known dental treatment units by the optical diagnostic arrangement in accordance with the invention shall be explained, firstly with reference to a tartar-removing unit as described in DE 83 22 850 U1. Only the most important elements of the tartar-removing unit shall be described here, since their functioning is already known sufficiently from the specification previously mentioned. The handpiece 30 that is shown in FIG. 10 has a pneumatically operable oscillation-generator 31 which is formed in order to set the instrument tip 32, held at the end of the grip sleeve 30, oscillating. The energy-supply line for the oscillation-generator 31 is formed by a compressed-air structure 34 that extends axially through the handpiece 30.

In accordance with the invention the known handpiece 30 can be supplemented by arranging the elements of the optical diagnostic device, namely the laser diode 2, the hemispherical lens 3, the fluorescence filter 5 and the photodiode 7 in a rear region of the handpiece. Provided for the purpose of transmitting the stimulating radiation and the fluorescent radiation there is a light-guide 33 which extends axially within the compressed-air line 34 through the handpiece 30 as far as the instrument tip 32 and there in a channel 35 extends as far as the end 36 that is directed at the tooth region to be treated. In this exemplary embodiment, the additional focussing lens has been dispensed with, since the curvature of the hemispherical lens 3 suffices in order to couple the stimulating radiation A into the light-guide 33. As can be inferred from the representation, the elements that are important for the optical diagnostic device can be accommodated in the handpiece 30 in a space-saving manner.

Figure 11A:
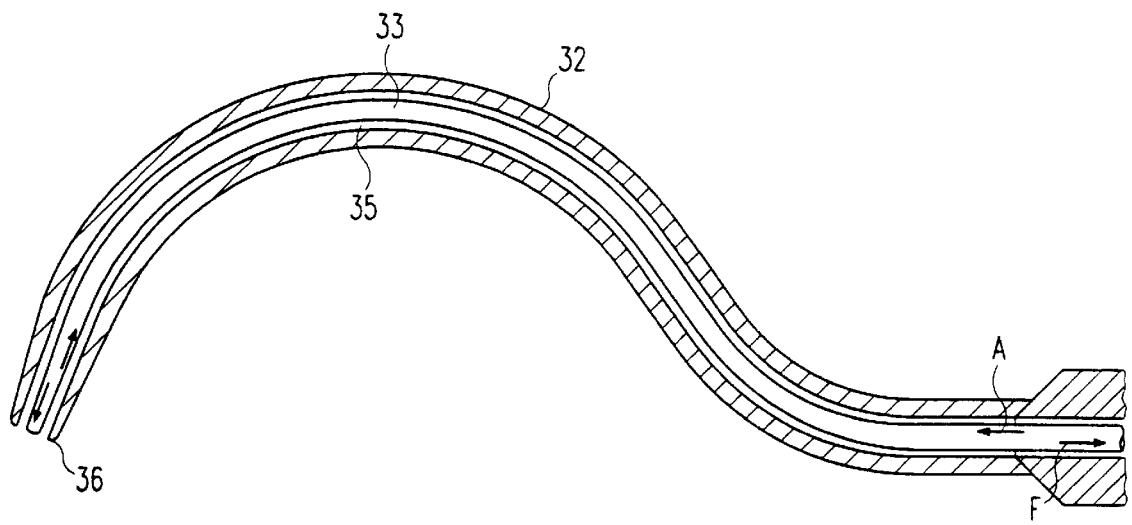
FIG. 11a shows the configuration of the tip of the instrument of the tartar-removing unit shown in FIG. 10.
Figure 11B:
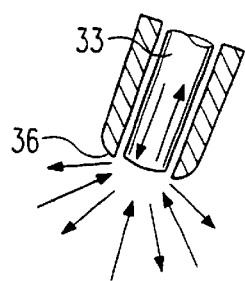
FIG. 11b shows an enlarged representation of the tip of the instrument.

The configuration of the instrument tip 32 is shown on an enlarged scale in FIGS. 11a and 11b. The light-guide 33 is preferably formed by means of very flexible fibre optical light-guides in order not to be damaged by the high-frequency oscillations of the tip 32. It extends through an elongated hollow space 35 of the instrument tip as far as the tip's end 36, but does not protrude beyond the latter in order not to be damaged during the treatment of the tooth-tissue region. The possibility exists here of using the channel 35 that extends in the instrument tip 32 in addition as well to transmit a cooling fluid or the like. It is important that the stimulating radiation A be directed precisely onto the tooth-tissue region that is being treated by the instrument tip 32.

The whole dental device has, furthermore, an indicating element which provides information on whether the tooth-tissue region, at which the instrument tip 32 is directed, is carious or loaded with concretions or films or not so that a user can proceed with therapeutic treatment in accordance with the result of diagnosis. Another possibility consists in triggering the actuation of the oscillation-generator 31 for the instrument tip 32 by way of a control unit in such a way that the treatment by means of the instrument tip 32 is effected automatically in accordance with the result of diagnosis by the optical diagnostic device.

Figure 12A:
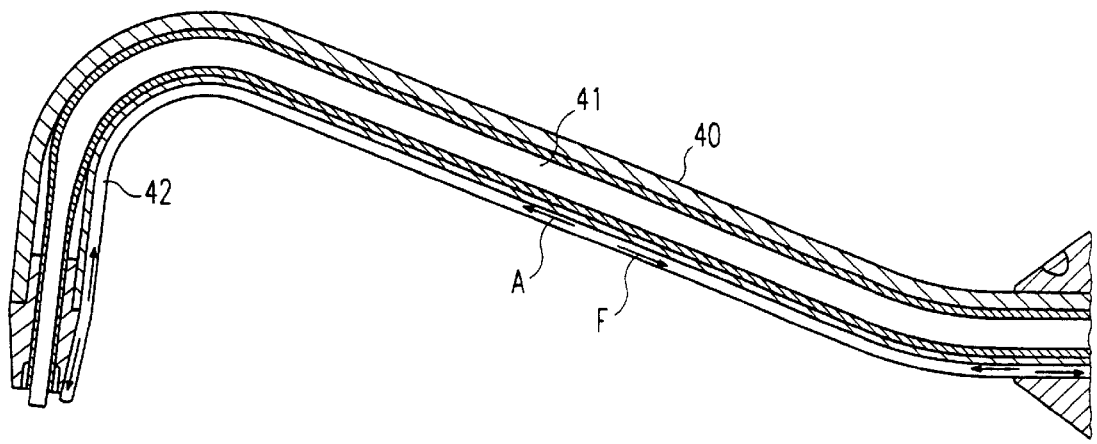
FIG. 12a shows the tip of the instrument of a further treatment unit that is extended by the optical diagnostic device.
Figure 12B:
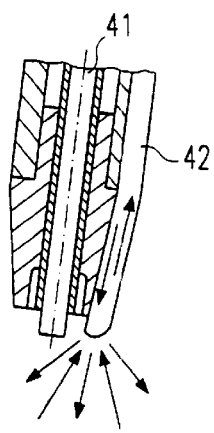

Finally, the supplement of a further known dental treatment unit by the optical diagnostic device shall be presented. The unit discussed in the following is a dental hand instrument in which an abrasive treatment agent is directed onto the tooth-tissue region that is to be treated, as described in detail, for example, in DE 197 42 701 A1. FIGS. 12a and 12b show the extension of the treatment tip in accordance with the invention. The arrangement of the further elements of the diagnostic device is effected analogously to the example of the tartar-removing unit previously described.

The instrument tip 40 in this case represents a cannula, by way of the internal channel 41 of which an abrasive treatment agent is directed onto a tooth-tissue region. In this case, it would be disadvantageous to arrange the light-guide 42 that is used for the transmission of the stimulating radiation A and the fluorescent radiation F within this channel 41, since the abrasive fluid would also damage the light-guide 42. In the present case therefore the light-guide 42 is arranged on the outside of the treatment tip, with in turn the stimulating radiation that is coupled out at the end of the light-guide 42 being directed precisely onto the region onto which the abrasive fluid is applied by way of the channel 41. In this example as well the possibility exists of adjusting the therapeutic function of the instrument as a function of the result of diagnosis either by means of an automatic control device or by means of a visual or acoustic display or indication of the result of diagnosis.

These two examples make it clear that it is easily possible to extend known treatment units by means of the effective optical diagnostic method and consequently form an extremely versatile dental unit. This is rendered possible in particular as a result of the fact that the dimensions can now be kept so small that the important elements of the optical diagnostic device can be integrated into a handpiece. Of course, the possibility also exists of accommodating the means for generating the stimulating radiation and for evaluating the fluorescent radiation in a separate base unit and of then transmitting the two types of radiation by way of a light-guide in a supply tube for the handpiece. Since the possibility exists, furthermore, of adjusting the therapeutic activity as a function of the state of the tooth region, substantially improved and more effective treatment of teeth surfaces can consequently be achieved.

Finally, it is also to be noted that basically even the arrangement of the laser diode and the photodiode (if applicable with the pertinent filter) can be interchanged, in which case the reflective coating is then to be realized on the rear side of the hemispherical lens in such a way that it reflects the fluorescent radiation. The arrangement shown in the drawing though is preferable on account of the fact that the coating which is required therefor can be produced more easily.

What is claimed is:

1. Device for identifying caries, plaque, bacterial infection, concretions, tartar and other fluorescent substances on teeth, having means for generating stimulating radiation, which is to be directed onto a tooth-tissue region that is to be investigated, and detection means and evaluation means for detecting and evaluating fluorescent radiation that is generated by the irradiated tooth-tissue region in response to the irradiation, with a beam splitter provided in the optical path between the means for generating the stimulating radiation and the tooth-tissue region that is to be investigated, wherein the beam splitter reflects the stimulating radiation in the direction of the tooth-tissue region and substantially lets through the fluorescent radiation, and wherein the beam splitter is formed by a planar rear side of a substantially hemispherical lens.

2. Device according to claim 1, further comprising a probe for periodontal diagnostics that is to be inserted into a tooth pocket of a tooth that is to be investigated, and a probe tip from which the stimulating radiation is coupled out and directed onto the tooth-tissue region that is to be investigated.

3. Device according to claim 2, wherein the probe consists of a light-guiding material and has the form of a periodontal probe, a cone or a light wedge.

4. Device according to claim 2, wherein the probe has markings or a scale on its outside.

5. Device according to claim 2, wherein the probe is mounted in a resilient manner in the axial direction.

6. Device according to claim 2, further comprising a flexible light-guide in order to couple the stimulating radiation into an end of the probe that lies opposite the probe tip.

7. Device according to claim 2, further comprising a mirror arranged in the optical path between the means for generating the stimulating radiation and the probe in order to couple the stimulating radiation into an end of the probe that lies opposite the probe tip.

8. Device according to claim 1, wherein the planar rear side of the hemispherical lens has a coating which reflects the stimulating radiation and substantially lets through the fluorescent radiation.

9. Device according to claim 1, further comprising a filter that is permeable only for the fluorescent radiation and that is arranged in the optical path between the hemispherical lens and the detection means.

10. Device according to claim 1, wherein the means for generating the stimulating radiation have a laser diode.

11. Device according to claim 1, wherein the detection means have a photodiode.

12. Device for identifying canes, plaque, bacterial infection, concretions, tartar and other fluorescent substances on teeth, having means for generating stimulating radiation which is to be directed onto a tooth-tissue region that is to be investigated, and detection means and evaluation means for detecting and evaluating fluorescent radiation that is generated by the irradiated tooth-tissue region in response to the irradiation, with a beam splitter provided in the optical path between the means for generating the stimulating radiation and the tooth-tissue region that is to be investigated, wherein the beam splitter reflects the stimulating radiation in the direction of the tooth-tissue region and substantially lets through the fluorescent radiation, and wherein the means for generating the stimulating radiation together with the beam splitter are integrated into a dental handpiece.

13. Device according to claim 12, wherein the beam splitter is formed by the planar rear side of a substantially hemispherical lens.

14. Device according to claim 12, further comprising a probe for periodontal diagnostics that is to be inserted into a tooth pocket of a tooth that is to be investigated, and a probe tip from which the stimulating radiation is coupled out and directed onto the tooth-tissue region that is to be investigated.

15. Device according to claim 14, wherein the probe consists of a light-guiding material and has the form of a periodontal probe, a cone or a light wedge.

16. Device according to claim 14, wherein the probe has markings or a scale on its outside.

17. Device according to claim 14, wherein the probe is mounted in a resilient manner in the axial direction.

18. Device according to claim 14, further comprising a flexible light-guide in order to couple the stimulating radiation into an end of the probe that lies opposite the probe tip.

19. Device according to claim 14, further comprising a mirror which is arranged in the optical path between the means for generating the stimulating radiation and the probe in order to couple the stimulating radiation into an end of the probe that lies opposite the probe tip.

20. Device according to claim 12, wherein the planar rear side of the hemispherical lens has a coating which reflects the stimulating radiation and substantially lets through the fluorescent radiation.

21. Device according to claim 12, further comprising a filter that is permeable only for the fluorescent radiation and that is arranged in the optical path between the hemispherical lens and the detection means.

22. Device according to claim 12, wherein the means for generating the stimulating radiation have a laser diode.

23. Device according to claim 12, wherein the detection means have a photodiode.

24. Dental device comprising:

a handpiece with an instrument tip for mechanical treatment of a tooth-tissue region;

means for generating stimulating radiation which is to be directed onto the tooth-tissue region that is to be treated by the instrument tip;

detection means for detecting fluorescent radiation that is generated at the irradiated tooth-tissue region to be treated in response to the irradiation;

evaluation means for diagnosing, with the aid of the intensity of the fluorescent radiation, a state of the irradiated tooth-tissue region that is to be treated; and a control device which controls mechanical treatment of the tooth-tissue region by the instrument tip as a function of a result of diagnosis.

25. Device according to claim 24, further comprising a visual or acoustic display or indicating device for indicating the intensity of the fluorescent radiation or a result of diagnosis.

26. Device according to claim 24, further comprising a light-guide that extends within or on an outside of the instrument tip in order to direct the stimulating radiation onto the tooth-tissue region that is to be treated.

27. Device according to claim 26, wherein the fluorescent radiation is transmitted by way of the same light-guide from the instrument tip to the detection means.

28. Device according to claim 24, further comprising a beam splitter provided in the optical path between the means for generating the stimulating radiation and the tooth-tissue region that is to be investigated, wherein the beam splitter reflects the stimulating radiation in the direction of the tooth-tissue region and substantially lets through the fluorescent radiation, and wherein the beam splitter is formed by a planar rear side of a substantially hemispherical lens.

29. Device according to claim 28, wherein the planar rear side of the hemispherical lens has a coating which reflects the stimulating radiation and substantially lets through the fluorescent radiation.

30. Device according to claim 28, further comprising a filter that is permeable only for the fluorescent radiation and that is arranged in the optical path between the hemispherical lens and the detection means.

31. Device according to claim 24, wherein the instrument tip has a supply line by way of which an abrasive treatment agent is directed onto the tooth-tissue region that is to be treated.

32. Device according to claim 24, further comprising an oscillation-generator by means of which the instrument tip is set oscillating for mechanical treatment of the tooth-tissue region.

33. Device according to claim 24, wherein the detection means have a photodiode.

34. Device according to claim 24, wherein the means for generating the stimulating radiation have a laser diode.

* * * * *

UNITED STATES PATENT AND TRADEMARK OFFICE
CERTIFICATE OF CORRECTION

PATENT NO. : 6,561,802 B2 Page 1 of 1
APPLICATION NO. : 09/810592
DATED : May 13, 2003
INVENTOR(S) : Alexander Hack It is certified that error appears in the above-identified patent and that said Letters Patent is hereby corrected as shown below:

Title Page, Item (12) Patentee:
Please delete "Alexander" and replace with --Hack--.

Title Page, Item (75) Inventors:
Please delete "Hack Alexander" and replace with --Alexander Hack--.

Signed and Sealed this

Twenty-ninth Day of June, 2010

David J. Kappos
*Director of the United States Patent and Trademark Office*